(12) United States Patent
Nagle

(10) Patent No.: US 6,225,107 B1
(45) Date of Patent: May 1, 2001

(54) TISSUE SPECIMEN CARRIER

(76) Inventor: Michael G. Nagle, 721 Moffet St., Joplin, MO (US) 64801

( * ) Notice: Subject to any disclaimer, the term of this patent is extended or adjusted under 35 U.S.C. 154(b) by 0 days.

(21) Appl. No.: 09/189,387

(22) Filed: Nov. 10, 1998

(51) Int. Cl.[7] .................................................. C12M 3/00
(52) U.S. Cl. .................................. 435/283.1; 435/307.1; 378/164; 378/208
(58) Field of Search ............................. 435/288.7, 283.1, 435/288.3, 307.1, 305.1, 305.4; 378/208, 68, 164; 250/491.1; 422/102, 104, 99, 101; 83/915.5

(56) References Cited

U.S. PATENT DOCUMENTS

| | | |
|---|---|---|
| 3,554,433 * | 1/1971 | Cardenaz . |
| 4,801,553 | 1/1989 | Owen et al. .......................... 436/174 |
| 5,002,735 * | 3/1991 | Alberhashy et al. ................... 422/99 |
| 5,223,405 | 6/1993 | Howell et al. .......................... 435/30 |
| 5,312,758 | 5/1994 | Ahlqvist .................................. 436/63 |
| 5,383,234 * | 1/1995 | Russell ................................. 376/164 |
| 5,427,742 | 6/1995 | Holland ................................ 422/102 |
| 5,550,033 | 8/1996 | Krumdieck ........................ 435/40.52 |
| 5,568,534 * | 10/1996 | Watkins ............................... 378/208 |
| 5,609,827 | 3/1997 | Russell et al. ....................... 422/102 |
| 5,781,608 * | 7/1998 | Tomie et al. ......................... 378/119 |
| 5,817,032 | 10/1998 | Williamson, IV et al. .......... 600/562 |

OTHER PUBLICATIONS

Silverstein, *Ductal Carcinoma in Situ*, Section 17, Pathology of Ductual Carconoma in Situ, p. 190–191, (1997).

* cited by examiner

Primary Examiner—William H. Beisner
(74) Attorney, Agent, or Firm—Wood, Herron & Evans, LLP

(57) ABSTRACT

A carrier and method of using to orient and maintain an excised tissue sample in an orientation sufficient to determine its position in a body. The carrier permits radiological and pathological evaluation of a precisely and accurately oriented tissue specimen. The carrier is comprised of an outer box open at a lateral end for receiving a specimen, and a slidably insertable inner box for containing and minimally compressing the specimen. The specimen is marked and maintained in its in vivo orientation from the time of excision and is evaluated for localization and orientation of a tumor during radiological and/or pathological assessment. The carrier and method increase the accuracy and efficiency of diagnosis and any subsequent treatment.

13 Claims, 2 Drawing Sheets

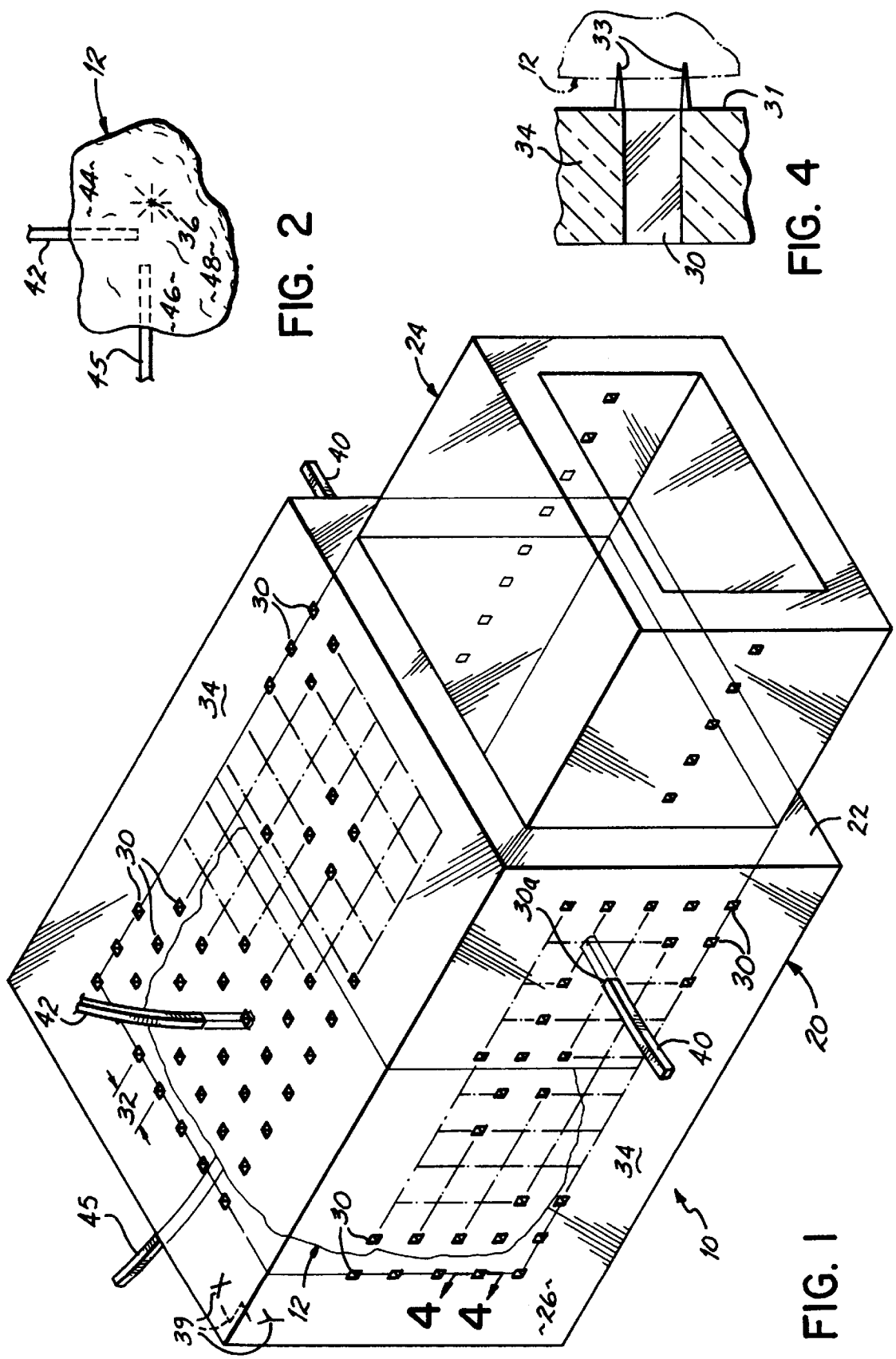

TISSUE SPECIMEN CARRIER

FIELD OF THE INVENTION

The invention relates to a carrier to maintain an excised tissue specimen such as a breast biopsy specimen in a defined and stable orientation throughout subsequent processing and evaluation.

BACKGROUND

Mammography is a noninvasive screening method for early detection of breast cancer. By pinpointing lesions as small as a few millimeters for further evaluation, mammography is an effective way to detect early-stage breast cancer, leading to increased treatment efficacy and decreased morbidity and mortality. The prevalence of mammography has led to increased follow-up evaluation including surgical biopsies of suspicious lesions or masses.

Among the diagnostic evaluation protocols, gross and microscopic pathological examination of excised suspicious tissues is routinely performed. This often consists of macroscopically examining the intact tissue, then histologically processing the tissue for subsequent microscopic evaluation of one or more stained serial sections. In addition, radiologic evaluation of the tissue, either in an intact form or in serial sections, may be performed.

In evaluating an excised tissue sample for the presence of malignant, pre-malignant or suspicious cells, it is useful if the tissue is maintained in an undistorted manner and in the exact orientation from which it was removed from the body. Maintaining tissue orientation permits a clinician to determine the extent of any malignancy that may be present; for example, if the tissue margins are free from malignant cells, the clinician is given greater assurance that the entire lesion was excised. This lessens the need for subsequent or more invasive surgery or other procedure. In contrast, if the tissue margins contain malignant, pre-malignant or suspicious cells, further surgery may be desirable to ensure that more or all of a mass is removed.

A variety of devices are available for securing and transporting such excised tissues for pathologic and/or radiologic evaluation. For example, tissue samples can be sandwiched and compressed between two plates, with the plates forming a grid for locating a mass within a tissue sample during subsequent radiological and pathological evaluation. As another example, tissue samples may be contained in carriers that have multiple compartments to contain core tissue samples as well as peripheral tissue samples to ensure the core tumor as well as the surrounding tissue is evaluated. As still another example, tissue samples may be contained in molds that vertically orient specimens prior to histological embedding and processing. None of these devices, however, minimize distortion of the tissue and maintain tissue orientation during transport and radiological and/or pathological evaluation so that, for example, accurate assessment of tissue margins may be made.

SUMMARY OF THE INVENTION

The invention is directed to a tissue specimen carrier that minimizes specimen distortion and maintains in vivo orientation of the tissue from excision throughout transport and radiological and/or pathological evaluation. The carrier is a radiographically transparent outer device or box to contain the tissue in a known fixed orientation, with the outer box open at at least one face for receiving a slidably insertable radiographically transparent inner device or box, and the inner box for securing the specimen contained in the outer box. In one embodiment, the carrier has a plurality of apertures at least one surface. The carrier may be appropriately sized to contain a tissue specimen that is in the range of, for example, about one to about five times smaller than the size of the carrier.

The invention also relates to a method of maintaining an excised tissue specimen in a defined and stable orientation relative to its orientation in the body throughout radiologic and/or pathologic evaluation. The specimen may be a breast biopsy specimen.

The invention additionally relates to a method of providing an oriented orthogonal view of an excised tissue from a body for subsequent diagnostic evaluation. The specimen is oriented relative to its location in the body, and is inserted into a carrier and maintained in the fixed oriented position throughout diagnosis.

The invention is also directed to a method of providing accurate radiographic margin assessment of an excised breast tissue specimen comprising orienting the excised tissue relative to its position in the body, inserting the oriented tissue into a carrier comprising an outer box open at at least one face end and a slidably insertable inner box, exerting a force on the inner box sufficient to conform the tissue roughly to a dimension of said outer box, and performing said assessment on the contained oriented tissue. The excised breast tissue may be obtained from a biopsy, a lumpectomy, or a mastectomy. These and other advantages of the invention will be further understood with reference to the following figures and detailed description.

BRIEF DESCRIPTION OF THE DRAWINGS

FIG. 1 is a perspective view of the tissue specimen apparatus containing an excised and oriented tissue specimen.

FIG. 2 is a perspective view of an oriented excised tissue specimen.

FIG. 4 is a cross-sectional view of the apparatus taken along line 4—4 of FIG. 1.

Detailed Description

Figure 3:
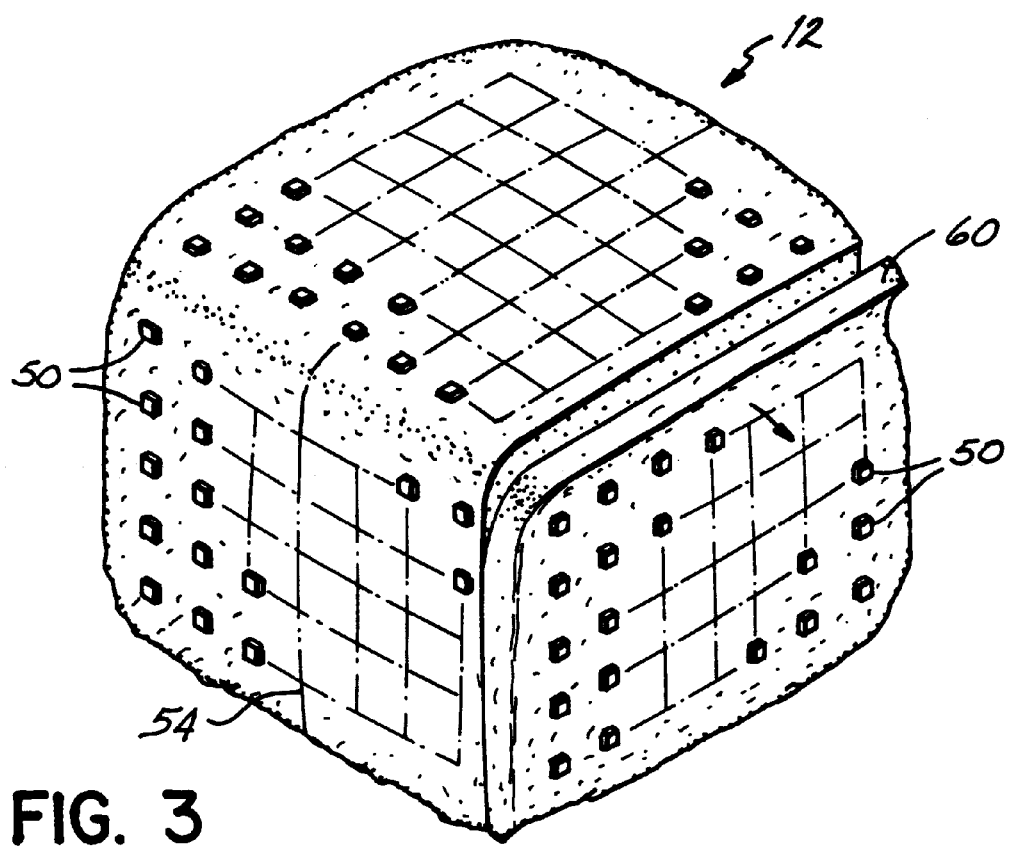
FIG. 3 is a perspective view of a tissue specimen prepared for sectioning.

As shown in FIG. 1, a carries apparatus or device 10 to contain and maintain a surgically excised tissue specimen 12 in a defined orientation relative to its removal from a body is disclosed. The excised tissue specimen 12 may be a biopsy or other specimen known or suspected of containing a tumor, lesion, cyst or mass of cells that requires further diagnostic or therapeutic evaluation or examination, for example, to determine if malignant, pre-malignant, suspicious or otherwise abnormal cells are present.

The carrier 10 comprises an outer compartment or box 20 that is open at at least one face 22 for stably containing and maintaining the excised specimen 12 in a known and fixed orientation, and a slidably insertable inner compartment or box 24 to secure and conform the specimen 12 contained therein. While a rectangular shaped box is preferable for ease of subsequent histological processing, the carrier 10 is not limited to this shape and may be, for example, square, circular or any other geometric shape. The outer box 20 and inner box 24 are preferably completely separable, but they may also form a unitary device with the outer box 20 and inner box 24 connected by, for example, a hinge or other connector. In one embodiment, a series of different sized carriers 10 are available to accommodate various sized biopsy specimens 12. A surgeon or practioner then selects the carrier 10 that is sized to either just accommodate a tissue specimen 12 or to contain a smaller-sized specimen 12. Preferably, the carrier 10 is sized to encompass specimens 12 ranging from about 2×2 cm to about 10×8 cm, and may range from about one to about five times the specimen 12 size.

The outer box 20 and inner box 24 are made of a radiographically transparent material 26. Examples of such radiographically transparent material 26 are extruded plastics, which may be either clear or colored. The edges or beams are preferably thin so the carrier 10 can be cut or otherwise easily opened during subsequent tissue processing. It is preferred that the material 26 is also visually transparent to allow gross inspection of the specimen 12 contained therein.

The material 26 may have an orientation marking system 39 stamped or otherwise applied thereon to allow the surgeon to select a marking 39 for a particular orientation. The marking system 39 may be a coordinate system such as an x, y, z coordinate system 39 with which medical personnel are familiar, or another system. The system 39 is preferably visible on radiographic films to allow the radiologist to maintain orientation of the specimen 12 while viewing the films.

As shown in FIG. 4, the interior surface 31 of the outer box 20 may have one or more projections or barbs 33. The barbs 33 are preferably located in a region of the inner surface 31 that will contact the specimen 12 and may serve to secure the specimen 12 in the carrier 10. The barbs 33 may be of any material but are preferably the same material 26 as the carrier 10 and can be configured to project inwardly from an aperture 30. The barbs 33 are preferably about 1–5 mm long and may terminate in a substantially pointed tip so that they contact a portion of specimen 12 to assist in securing the specimen 12 in the carrier 10. In this embodiment, a contact of about one to a few mm into the specimen 12 is sufficient as long as the barb 33 catches or hooks into a portion of the specimen 12. In an alternative embodiment, the barbs do not hook into the specimen 12 but provide an external barrier to movement of the specimen 12 within the outer box 20.

The apparatus 10 is configured so that the material 26 defines a plurality of apertures 30, preferably having a square shape and preferably sized to accommodate a monofilament suture. The aperture 30 size is preferably in the range of about 1 mm to about 9 mm. The apertures 30 are preferably regularly spaced 32 to form grids of about 1 cm and are preferably present through each face 34 of the outer box 20 and through at least two opposing faces of the inner box 24.

With reference to FIG. 2, in use, a tissue sample 12 is excised from the body and is placed in the outer box 20 in the exact orientation from which it was located in and removed from the body. The tissue sample frequently is suspected of containing or may in fact be known to contain a tumor, mass, lesion, or cluster of suspicious or abnormal cells 36. The sample 12 may be, for example, breast tissue obtained by ultrasonographic or stereotactic guided core excision, excision preceded by insertion of a wire under mammographic guidance for localization of an impalpable abnormal shadow or microcalcification (needle localization biopsy), lumpectomy of a defined or palpable mass or from a partial or total mastectomy. The method and device, however, are not limited to use with breast tissue specimens and may be used with any excised solid tissue specimen, preferably requiring orientation with further evaluation such as a cyst or a solid organ specimen, for example, a liver biopsy specimen.

The invention permits a tissue specimen 12 to be accurately and fixedly maintained in the exact orientation as it was located and positioned in vivo. The excised specimen 12 is initially oriented by marking the specimen 12, usually visually marking using any convenient means such as placing any type of device or combination of devices such as pins, clips, sutures, etc. on or into the specimen 12. In one embodiment, the specimen 12 is oriented by placing sutures 40 of varying lengths at one or more defined positions in the specimen 12. For example, a shorter suture 42 may be placed at the superior extreme 44 of the specimen 12, and a longer suture 45 may be placed at a lateral extreme 46 of the specimen 12.

The specimen 12 thus oriented is placed into the outer box 20 of the carrier 10. It is particularly convenient to place the specimen 12 into the carrier 10 by grasping the specimen 12 by its anterior surface 48 and placing it into the carrier 10 by inserting the specimen 12 through at least one open face 22 so that its superior extreme 44 is oriented to the craniocaudacad (CC) face and the lateral extreme 48 is oriented to the mediolateral (ML) face.

A device 10 is selected from among a plurality of different-sized devices to either just accommodate the specimen 12 or to be in the range of preferably about one to five times larger than the specimen 12. An appropriately sized device 10 permits fixed and stable transport of a specimen 12. However, it will be appreciated that while a carrier 10 that is sized to be in the range of about one to about five times as large as the specimen 12 is preferred, any carrier 10 that is either the same size or larger than the specimen 12 may be used.

The interior compartment or box 24 is then inserted into the outer box 20 and is adjusted to stably contain the specimen 12 within the outer box 20. This is most easily accomplished by exerting a minimal compressive force, preferably by hand, on a surface of the inner box 24 sufficient for the inner box 24 to touch the outer surfaces of the specimen 12. A minimally compressive force is one that serves to substantially conform the specimen 12 to at least one surface of the inner box and to preferably form the specimen 12 in a substantially rectangular shape. This shape aids in subsequent tissue processing. The force further fixedly maintains the oriented tissue specimen 12 within the device 10, and also textures or nubs 50 the specimen surface. Sufficient texturing or nubbing on the surface of the specimen 12 is achieved by the regularly spaced, preferably square shaped apertures 30 and facilitates free-hand serial sectioning of the specimen 12.

After orientation of the specimen 12 is verified, the specimen 12 is secured within the inner box 24. This may be accomplished as the specimen 12 contacts the barbs 33 that inwardly project on an interior surface 31 of the outer box 20. This may additionally or alternatively be accomplished by inserting a suture 40 through an aperture 30 of the outer box 20 so that the suture 40 is inserted into the specimen 12. The inner box 24 is further secured in the outer box 20. In one embodiment, the inner box 24 is secured by an additional securing means, for example, by a straight suture 40 inserted through apertures 30a, 30b (not shown) in both the inner box 24 and outer box 20.

The specimen 12 that is oriented and fixed in an appropriately sized carrier 10 is then subjected to radiography. For example, the carrier 10 is placed against a photographic film and is exposed to x-rays. Radiographic films are obtained in both the CC and ML projections, corresponding to the orientation of any suspected lesion or mass 36 visualized on the film. Ideally, both the radiologist and surgeon view the film and may consult to determine whether to excise additional tissue. Additional tissue would likely be required if, for example, the film showed that the margins of the excised tissue 12 contained a suspicious or abnormal area or shadow.

The specimen 12, still maintained in an oriented and fixed position in the appropriately sized carrier 10, is then subjected to pathological evaluation. The carrier 10 may be transported for pathological evaluation by any timely means that will not compromise the specimen 12 orientation and integrity. The specimen 12 stably maintained in the carrier 10 is then subjected to histological processing. For example, the specimen 12 may be treated to cause tissue fixation and render the cellular structural components insoluble by immersing the carrier 10 containing the specimen 12 in a rapid fixation system solution such as a solution of 70–30 formyl alcohol (formalin 70% and isopropanol 30%) for at least four hours and up to about 18 hours.

With reference to FIG. 3, after fixation the specimen 12 having roughly a rectangular shape and a nubbed surface is removed while still maintaining orientation. Removal of the specimen 12 may be by any means that maintains orientation and integrity of the specimen 12. For example, the specimen 12 may be removed by grasping a laterally placed suture 45, either directly or using a device such as forceps or a hemostat, and applying gentle force to dislodge the specimen 12 from the carrier 10. As another example, the specimen 12 may be removed by cutting through the carrier 10, for example, at a thin edge, using any appropriate cutting tool such as a scalpel or scissors.

The specimen 12 is then immediately coded to differentiate each surface 44, 46, 48. This may be done, for example, by painting each surface 44, 46, 48 of the specimen 12 with a different colored ink and fixing the ink with a chemical mordant.

The specimen 12 is then sectioned in accordance with standard pathologic technique, for example, in a sagittal plane for subsequent processing. The fixed tissue specimen 12 is embedded or infiltrated with a solution of paraffin or other solution that solidifies so that the tissue and the embedding matrix may be sectioned together. The fixed, ordered and oriented sections 60 may be further evaluated radiologically. This would be of use, for example, in the case where microcalcifications, an early indicator of tumor formation in breast tissue, were noted and required closer evaluation. Alternatively or additionally, the sections 60 may be placed in cassettes or other types of suitable packaging for further histological processing such as staining for pathological evaluation.

It should be understood that the embodiments of the present invention shown and described in the specification are only preferred embodiments of the inventor and are not limiting in any way. Therefore, various changes, modifications or alterations to these embodiments may be made or resorted to without departing from the spirit of the invention and the scope of the following claims.

What is claimed is:

1. A tissue specimen carrier comprising a radiographically transparent outer box for stably containing an excised tissue specimen in a known fixed orientation, said outer box having at least one inward projection to further secure said specimen and open at at least one face for receiving a slidable insertable radiographically transparent inner box, and said slidably insertable radiographically transparent inner box for minimally compressibly securing said specimen contained in said outer box.

2. The carrier of claim 1 having a plurality of apertures on at least one surface of said outer box.

3. A tissue specimen carrier comprising a radiographically transparent outer box for stably containing an excised tissue specimen in a known fixed orientation, said outer box having a plurality of apertures defining a grid on at least one surface and at least one inward projection to further secure said specimen and open at at least one face for receiving a slidable insertable radiographically transparent inner box for minimally compressible securing said specimen contained in said outer box.

4. The carrier of claim 3 wherein said apertures are regularly spaced.

5. The carrier of claim 3 wherein said apertures define a grid of about 1 cm.

6. The carrier of claim 3 wherein said apertures are square.

7. The carrier of claim 3 wherein said compression by said inner box is sufficient to conform said specimen to at least one dimension of said outer box.

8. The carrier of claim 3 wherein said outer box further comprises an orientation marking system.

9. The carrier of claim 3 having a size in the range of about one to about five times the size of said specimen.

10. The carrier of claim 3 wherein said outer box and said inner box are unitary.

11. The carrier of claim 3 wherein said outer box and said inner box are separable.

12. The carrier of claim 3 wherein said inner box is secured to said outer box.

13. The carrier of claim 3 where the specimen is excised from breast tissue.

* * * * *

UNITED STATES PATENT AND TRADEMARK OFFICE
CERTIFICATE OF CORRECTION

PATENT NO. : 6,225,107 B1
DATED : May 1, 2001
INVENTOR(S) : Michael G. Nagle

It is certified that error appears in the above-identified patent and that said Letters Patent is hereby corrected as shown below:

<u>Claim 3,</u>
Line 28, change "compressible" to -- compressibly --.

Signed and Sealed this

Twenty-seventh Day of November, 2001

Attest:

*Nicholas P. Godici*

NICHOLAS P. GODICI
*Acting Director of the United States Patent and Trademark Office*

*Attesting Officer*